United States Patent
Polman

(10) Patent No.: US 7,342,033 B2
(45) Date of Patent: *Mar. 11, 2008

(54) USE OF RILUZOLE FOR THE TREATMENT OF MULTIPLE SCLEROSIS

(75) Inventor: Chris Polman, Overveen (NL)

(73) Assignee: Vereniging Voor Christelijk Wetenschappelijk Onderwijs (NL)

(*) Notice: Subject to any disclaimer, the term of this patent is extended or adjusted under 35 U.S.C. 154(b) by 0 days.

This patent is subject to a terminal disclaimer.

(21) Appl. No.: 11/089,668

(22) Filed: Mar. 25, 2005

(65) Prior Publication Data

US 2005/0171168 A1   Aug. 4, 2005

Related U.S. Application Data

(62) Division of application No. 09/926,693, filed as application No. PCT/IB00/00933 on Jun. 2, 2000, now Pat. No. 6,872,739.

(60) Provisional application No. 60/174,328, filed on Jan. 4, 2000.

(30) Foreign Application Priority Data

Jun. 4, 1999   (EP)   ................................. 99201788

(51) Int. Cl.
*A61K 31/428* (2006.01)

(52) U.S. Cl. ................................... 514/367
(58) Field of Classification Search ................ 514/367
See application file for complete search history.

(56) References Cited

U.S. PATENT DOCUMENTS

| 4,826,860 A |   | 5/1989 | Johnson et al. ............. 514/367 |
| 5,236,940 A |   | 8/1993 | Audiau et al. .............. 514/367 |
| 5,668,117 A | * | 9/1997 | Shapiro ....................... 514/55 |
| 5,780,489 A | * | 7/1998 | Brooks ........................ 514/369 |
| 6,245,791 B1 |   | 6/2001 | Bohme et al. ............... 514/367 |
| 6,387,936 B1 |   | 5/2002 | Blanchard Bregeon et al. ........................... 514/367 |
| 6,872,739 B1 | * | 3/2005 | Polman ....................... 514/367 |
| 2003/0077641 A1 | * | 4/2003 | Laskowitz et al. ............. 435/6 |

FOREIGN PATENT DOCUMENTS

| EP | 0 558 861 A |   | 9/1993 |
| WO | WO 93/17683 A |   | 9/1993 |
| WO | 98/41882 | * | 9/1998 |
| WO | WO 98/41882 |   | 9/1998 |
| WO | WO 99/51097 |   | 1/1999 |
| WO | WO 99/47692 |   | 9/1999 |
| WO | WO 00/54773 |   | 9/2000 |
| WO | WO 01/95907 |   | 12/2001 |

OTHER PUBLICATIONS

Harvey, A.L., Med. Res. Rev. (13, No. 1, 81-104, 1993) (abstract).*
Harvard Women's Health Watch Newsletter (Feb. 1, 1998), vol. 5.*
The Merck Index (1999), 17th edition, pp. 1474-1476.*
Kalkers "A pilot study of riluzole in primary progressive multiple sclerosis; effect on spinal cord atrophy on MRI" 9th *Meeting of the European Neurological Society* Poster P419, Abstract (1999).
McCready "Rilutek might be tried for MS" *MS Pathfinder* Abstract (1998).
Schluep et al. *Medecine et Hygiene* 55/2145:33-35 Abstract (1997).
Stankoff "Neuroprotection and Central Nervous System myelination: New prospects for multiple sclerosis?" *Neurology* 52(6):A402 Abstract (1999).
Kalkers et al., "The effect of the neuroprotective agent riluzole on MRI parameters in primary progressive multiple sclerosis: a pilot study" *Multiple Sclerosis* 8:532-533 (2002).
Harvey, "Neuropharmacology of Potassium Ion Channels" *Medicinal Research Reviews* 13(1):81-104 (Jan. 1993).
*Harvard Women's Health Watch*, vol. V, No. 6 (Feb. 1998).

* cited by examiner

*Primary Examiner*—Phyllis G. Spivack
(74) *Attorney, Agent, or Firm*—Fish & Richardson P.C.

(57) ABSTRACT

Methods and compositions for the treatment of multiple sclerosis comprising riluzole (6-(trifluoromethoxy)-benzothiazolamine) are disclosed herein.

19 Claims, No Drawings

US 7,342,033 B2

USE OF RILUZOLE FOR THE TREATMENT OF MULTIPLE SCLEROSIS

CROSS REFERENCE TO RELATED APPLICATIONS

This application is a divisional application under 35 U.S.C. §120 of U.S. Patent application No. 09/926,693, filed Feb. 1, 2002 now U.S. Pat No. 6,872,739, which is a national stage application under 35 U.S.C. § 371 of International Patent Application No. PCT/IB00/00933, filed Jun. 2, 2000, which claims priority to U.S. Provisional patent application No. 60/174,328, filed Jan. 4, 2000, and European Patent Application No. 99201788.9, filed Jun. 4, 1999. The entire contents of each prior application are herein incorporated by reference.

The present invention relates to methods for treating multiple sclerosis and to methods of preparation of pharmaceutical compositions to be used for the treatment of multiple sclerosis.

BACKGROUND

Multiple sclerosis (MS) is an inflammatory demyelinating disease of the central nervous system (CNS). It is a major cause of disability, because in most patients the disease ultimately has a progressive course. In most patients, the progressive course of the disease manifests itself during or after a preceding phase of relapses and remissions (secondary progressive (SP) disease), whereas in a small percentage of patients (10-15%) the disease course is progressive from onset (primary progressive (PP) disease). Most currently available treatments for multiple sclerosis are aimed at suppressing the inflammatory component of the disease. Their main clinical impact is on relapses whereas an effect on permanent disability is less well established. Patients with PPMS show less inflammatory activity, which is one of the reasons why they are frequently excluded from treatment trials, despite clear clinical progression. Recent evidence sugggests that axonal loss may occur earlier in the disease course of MS than previously anticipated; it may be the pathologic correlate of irreversible disability.

MS is frequently characterized by plaques or lesions of demyelination in the nerve fibers of the brain and spinal cord. Demyelination causes multiple and varied neurologic symptoms and signs, usually with relapses and exacerbations.

The clinical course of MS is highly variable and unpredictable, with many patients experiencing acute episodes of exacerbations, followed by periods of remission. The disease progresses at various paces to a chronic, degenerative condition. Frequently, a diagnosis of MS may not be made for many years after the onset of symptoms because the symptoms can be variable, sporadic, and similar to those associated with other disorders. As the disease progresses, patients are frequently unable to remain fully ambulatory, and their functional systems steadily decline. The most severe cases of MS are characterized by paralysis or even death.

MS may occur in several forms classified as primary progressive, relapsing-remitting, and secondary progressive, depending on the pathophysiology, progression and severity of the symptoms.

There are several theories about the causes of MS, however, the precise causes of MS are not yet known. Research to date has indicated that the etiology of MS may in fact be related to a combination of factors, such as autoimmunity, environmental, viral and genetic factors.

Riluzole(6-trifluoromethoxy)-2-benzothiazolarnine) is described in European Patent 50,511 and US Pat. 4,370,338. Its use in the treatment of motor nerve diseases is described in European Patent 558,861. Riluzole is produced by Rhone-Poulenc Rorer (RPR) and is used for the treatment of amyotrophic lateral sclerosis (ALS), a disease unrelated to MS.

There remains a need to identify additional treatments for MS which can treat the disease, minimize the effects of the disease, or slow the progression of the disease.

SUMMARY OF THE INVENTION

The present invention results from the novel and surprising discovery that riluzole is useful in the preparation of pharmaceutical compositions for the treatment of all forms of multiple sclerosis. Thus, in various embodiments discussed herein, the presently claimed invention relates to the use of riluzole for preparing a pharmaceutical composition suitable for the treatment of multiple sclerosis, and methods for the treatment of multiple sclerosis, comprising administering to a patient in need of such treatment a pharmaceutical composition comprising a therapeutically effective amount of riluzole. The methods of treatment and methods of preparing pharmaceutical compositions disclosed herein may include not only riluzole, but also riluzole in combination with a pharmaceutical composition comprises a pharmaceutically effective carrier.

In yet other embodiments, the claimed invention relates to pharmaceutical compositions comprising a therapeutically or prophylactically effective amount of riluzole in combination with an additional agent having pharmaceutical properties. The additional agent can be any agent deemed useful by one skilled in the art in treating MS, or ameliorating or inhibiting the symptoms of MS, including, but not limited to, Type I interferons such as interferon beta-1b, copaxone, interferon beta-1a, muscle relaxants, anti-depressants, or immunosuppressants. Additionally, the claimed invention relates to methods of treatment of patients suffering from MS by administering an effective amount of such combinations to patient in need thereof.

In certain embodiments, the claimed compositions are administered in an amount of between about 10 and about 500 mg per day, more preferably, between about 50 and about 250 mg per day. Similarly, the preferred methods comprise administering these same dosages.

In yet other embodiments, the claimed invention relates to methods of inhibiting, minimizing or delaying the development of spinal cord atrophy associated with MS by administering an effective amount of riluzole, or riluzole in combination with a second agent as discussed above. The presently claimed invention relates to all types of MS, including those known, and types yet to be categorized. In various embodiments, the claims relate to methods for the treatment of a patient suffering from primary progressive MS, secondary progressive MS, and or relapsing-remitting MS comprising administering to said patient a therapeutically effective amount of a pharmaceutical composition comprising riluzole.

It is to be understood that both the foregoing general description and the following detailed description are exemplary and explanatory and are intended to provide further explanation of the invention as claimed. Reference will now be made in detail to the present preferred embodiments of the invention, examples of which are set forth herein.

DISCUSSION

As mentioned above, most currently available treatments for MS are aimed at suppressing the inflammatory component of the disease. Their main clinical impact is on relapses, whereas an effect on permanent disability has so far been less well established. The claimed invention relates to the use of riluzole in the treatment of multiple sclerosis. Riluzole, as used herein, refers to (6-trifluoromethoxy)-2-benzothiazolamine) as described in European Patent 50,511 and U.S. Pat. No. 4,370,338, as well as all analogs, homologs or variants thereof which have substantially the same activity and structure as riluzole.

The compositions of the invention can be made by methods known to those skilled in the art. Simply stated, riluzole can be prepared by the action of potassium thiocyanate and bromine on 4-triflouromethoxy-aniline in acetic acid medium. Preferred methods of preparation can be determined by those skilled in the art depending upon the desired economics and simplicity of process.

As used herein, the claimed pharmaceutical compositions may comprise a therapeutically effective amount of 6-(trifluoromethoxy)-2-benzothiazoloamine), its analogs, homologs, variants or salts thereof. Specifically, the present invention encompasses pharmaceutical compositions comprising pharmaceutically acceptable salts derived from inorganic or organic acids and bases.

The claimed methods can be used in the treatment of patients suffering from MS at any time in the progression of the disease, and may be used to treat patients suffering from primary progressive MS, secondary progressive MS, and/or relapsing remitting MS. It is preferred to use the claimed methods for the treatment of primary progressive MS.

The claimed invention in certain embodiments may act through the inhibition of glutamate transmission, an excitotoxin participating in the process of neuronal damage.

In various embodiments the claimed methods can encompass the administration of a therapeutically effective amount of riluzole alone, or in combination with another therapeutic or prophylactic agent. By administration in combination, it is meant that riluzole can be administered either substantially simultaneously with the second agent, or that the second agent can be administered in a stepwise fashion with riluzole. Thus, in various embodiments, depending on the particular treatment regime chosen by the physician, one may administer riluzole at the same time as the second agent, or in other embodiments, riluzole and the second agent can be administered hours, days, or possibly even weeks apart. The desired treatment regime can be easily determined by one skilled in the art depending upon the particulars of the patient being treated, and the desired outcome.

Any therapeutic or prophylactic agent useful in the treatment of MS or any of its associated symptoms may be used as the second agent according to this invention. In preferred embodiments, the second agent is selected from the type I interferons, more preferably, interferon beta-1a. Additionally, however, other second agents can be used in the claimed invention, including, but not limited to steroids, pain relievers, muscle relaxants, immunosuppressants and copaxone.

The compounds of the present invention may be formulated into pharmaceutical compositions that may be administered orally, parenterally, such as, for example, retrobulbar administration, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective to prevent, suppress or inhibit cell adhesion will depend on a variety of factors, such as the nature of the inhibitor, the size of the patient, the goal of the treatment, the nature of the pathology to be treated, the specific pharmaceutical composition used, and the judgment of the treating physician. Dosage levels of between about 10 and about 500 mg per day, preferably between about 25 to 250 mg per day, and most preferably, between about 100 to 150 mg per day of riluzole are useful.

EXAMPLE 1

We selected 9 women and 7 men (aged 30-66 years) with documented progression during the 24 months before inclusion, from a natural history study. Kurtzke's EDSS scores were between 3.0 (inclusive) and 7.5 (inclusive). All adverse events were documented; safety lab consisted of serum transaminases (monthly for 3 months and every 3 months thereafter) and hematology (CBC and differential every 6 months) after the start of treatment. The study was approved by the hospital ethics committee, and all patients gave informed consent. During the first year no specific treatment was given; during the second year all patients were treated with riluzole (2×50 mg daily). MRI scanning consisted of a 6-monthly inversion prepared 3D gradient echo sequence of the cervical cord, and yearly T1- and T2-weighted spin-echo sequences of the brain. The main efficacy parameter was the change in spinal cord cross-sectional area, obtained from 10 contiguous 3-mm axial slices perpendicular to the cord above the center of the C2-C3; the coefficient of variation for this method in our hands was 1.3%. Scans were analysed in a randomized and blinded fashion.

RESULTS

Two patients discontinued treatment because of side effects (headache in one, increase in spasticity in the other). Five patients needed intermittent reduction in dosage of study drug. In 14 patients who took medication for over three months, medically severe adverse effects were not observed. Adequate MRI data could not be obtained at multiple time points in one patient, while five others had one missing data point. As shown in Table 1 a clear reduction (2%) in cord area (p=0.59) in the first year was found, and an increase in T1 and T2 lesion loads, as expected. In the second year we saw a stabilisation in cord diameter (−0.15%), see FIG. 1. The increase in T2 lesion load in the brain did not alter much under treatment, but the accumulation of hypointense lesion showed a trend towards reduction (p=0.66). No effect on EDSS score was seen.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

TABLE 1

Baseline data for spinal cord area, T1 and T2 lesion load, the increase in year without and with treatment and with respective 95% confidence interval (CI)

| MRI parameter | Baseline | ☐ 0-1 yr | ☐ 1-2-yr | difference ☐ 0-1 yr versus ☐ 1-2-yr |
|---|---|---|---|---|
| Spinal cord area[1] | 66.7 mm$^2$ | −1.3 mm$^2$ (−2%) CI: −4.5 to 3.5% | −0.2 mm$^2$ (−0.15%) CI: −4.0 to 2.4% | −1.5 mm$^2$ (−2.15%) CI: −4.8 to 4.9% |
| T1 lesion load[2] | 271.5 mm$^3$ (0.0-7032.0) | median 15% mean 27% CI: −9.3 to 63% | median 6% mean 24% CI: −2.1 to 51% | median 24% mean 53% CI: 2.1 to 104% |
| T2 lesion load[2] | 2160.0 mm$^3$ (513.0-32892.0) | median: 7% mean 13%: CI: −3.5 to 30% | median: 10% mean 12% CI: −3.8 to 29% | median 21.6% mean 28% CI: −2.1 to 54% |

[1]mean in mm$^2$ (SD);
[2]median (range)

What is claimed is:

1. A method for the treatment of multiple sclerosis, the method comprising administering to a patient suffering from multiple sclerosis:

(a) a first pharmaceutical composition comprising a therapeutically effective amount of a first agent that is 6-(trifluoromethoxy)-2-benzothiazolamine or a salt thereof; and (b) a second pharmaceutical composition comprising a therapeutically effective amount of a second agent selected from the group consisting of steroids, pain relievers, muscle relaxants, and immunosuppressants.

2. The method of claim 1 further comprising administering to the patient a therapeutically effective amount of a third agent.

3. The method of claim 2 wherein the third agent is selected from the group consisting of interferon beta-1a, interferon beta-1b, and copaxone.

4. The method of claim 1 wherein the amount of 6-(trifluoromethoxy)-2-benzothiazolamine or the salt thereof administered to the patient is between about 10 and about 500 mg per day.

5. The method of claim 4 wherein the amount of 6-(trifluoromethoxy)-2-benzothiazolamine or the salt thereof administered to the patient is between about 50 and about 250 mg per day.

6. The method of claim 1 wherein the second agent is a steroid.

7. The method of claim 1 wherein the second agent is a pain reliever.

8. The method of claim 1 wherein the second agent is a muscle relaxant.

9. The method of claim 1 wherein the second agent is an immunosuppressant.

10. The method of claim 1 wherein the patient is suffering from primary progressive multiple sclerosis.

11. The method of claim 10 further comprising administering to the patient a third agent.

12. The method of claim 11 wherein the third agent is selected from the group consisting of interferon beta-1b, copaxone and interferon beta-1a.

13. The method of claim 10 wherein the first pharmaceutical composition comprises 6-(trifluoromethoxy)-2-benzothiazolamine.

14. The method of claim 1 wherein the patient is suffering from secondary-progressive multiple sclerosis.

15. The method of claim 1 wherein the patient is suffering from relapsing-remitting multiple sclerosis.

16. The method of claim 1 wherein the first pharmaceutical composition comprises 6-(trifluoromethoxy)-2-benzothiazolamine.

17. The method of claim 1 wherein the first and second pharmaceutical compositions are administered substantially simultaneously.

18. The method of claim 1 wherein the first and second pharmaceutical compositions are administered in a stepwise fashion.

19. The method of claim 1 wherein the first and second pharmaceutical compositions are formulated as a single composition.

* * * * *

UNITED STATES PATENT AND TRADEMARK OFFICE
CERTIFICATE OF CORRECTION

PATENT NO. : 7,342,033 B2
APPLICATION NO. : 11/089668
DATED : March 11, 2008
INVENTOR(S) : Chris Polman It is certified that error appears in the above-identified patent and that said Letters Patent is hereby corrected as shown below:

<u>Column 7</u>
Claim 2, Line 1, after "1" and before "further" insert -- , --

<u>Column 7</u>
Claim 3, Line 1, after "2" and before "wherein" insert -- , --

<u>Column 7</u>
Claim 4, Line 1, after "1" and before "wherein" insert -- , --

<u>Column 7</u>
Claim 5, Line 1, after "4" and before "wherein" insert -- , --

<u>Column 7</u>
Claim 6, Line 1, after "1" and before "wherein" insert -- , --

<u>Column 7</u>
Claim 7, Line 1, after "1" and before "wherein" insert -- , --

<u>Column 7</u>
Claim 8, Line 1, after "1" and before "wherein" insert -- , --

<u>Column 7</u>
Claim 9, Line 1, after "1" and before "wherein" insert -- , --

<u>Column 7</u>
Claim 10, Line 1, after "1" and before "wherein" insert -- , --

<u>Column 7</u>
Claim 11, Line 1, after "10" and before "further" insert -- , --

<u>Column 8</u>
Claim 12, Line 1, after "11" and before "wherein" insert -- , --

<u>Column 8</u>
Claim 13, Line 1, after "10" and before "wherein" insert -- , --

<u>Column 8</u>
Claim 14, Line 1, after "1" and before "wherein" insert -- , --

UNITED STATES PATENT AND TRADEMARK OFFICE
CERTIFICATE OF CORRECTION

PATENT NO. : 7,342,033 B2
APPLICATION NO. : 11/089668
DATED : March 11, 2008
INVENTOR(S) : Chris Polman It is certified that error appears in the above-identified patent and that said Letters Patent is hereby corrected as shown below:

Column 8
Claim 15, Line 1, after "1" and before "wherein" insert -- , --

Column 8
Claim 16, Line 1, after "1" and before "wherein" insert -- , --

Column 8
Claim 17, Line 1, after "1" and before "wherein" insert -- , --

Column 8
Claim 18, Line 1, after "1" and before "wherein" insert -- , --

Column 8
Claim 19, Line 1, after "1" and before "wherein" insert -- , --

Signed and Sealed this

Thirteenth Day of January, 2009

JON W. DUDAS
*Director of the United States Patent and Trademark Office*

UNITED STATES PATENT AND TRADEMARK OFFICE
CERTIFICATE OF CORRECTION

PATENT NO.      : 7,342,033 B2
APPLICATION NO. : 11/089668
DATED           : March 11, 2008
INVENTOR(S)     : Chris Polman It is certified that error appears in the above-identified patent and that said Letters Patent is hereby corrected as shown below:

Column 7
Claim 2, Line 1, after "1" and before "further" insert -- , --

Column 7
Claim 3, Line 4, after "2" and before "wherein" insert -- , --

Column 7
Claim 4, Line 7, after "1" and before "wherein" insert -- , --

Column 7
Claim 5, Line 11, after "4" and before "wherein" insert -- , --

Column 7
Claim 6, Line 15, after "1" and before "wherein" insert -- , --

Column 7
Claim 7, Line 17, after "1" and before "wherein" insert -- , --

Column 7
Claim 8, Line 19, after "1" and before "wherein" insert -- , --

Column 7
Claim 9, Line 21, after "1" and before "wherein" insert -- , --

Column 7
Claim 10, Line 23, after "1" and before "wherein" insert -- , --

Column 7
Claim 11, Line 25, after "10" and before "further" insert -- , --

Column 8
Claim 12, Line 1, after "11" and before "wherein" insert -- , --

Column 8
Claim 13, Line 4, after "10" and before "wherein" insert -- , --

Column 8
Claim 14, Line 8, after "1" and before "wherein" insert -- , --

UNITED STATES PATENT AND TRADEMARK OFFICE
CERTIFICATE OF CORRECTION

PATENT NO. : 7,342,033 B2
APPLICATION NO. : 11/089668
DATED : March 11, 2008
INVENTOR(S) : Chris Polman It is certified that error appears in the above-identified patent and that said Letters Patent is hereby corrected as shown below:

Column 8
Claim 15, Line 10, after "1" and before "wherein" insert -- , --

Column 8
Claim 16, Line 12, after "1" and before "wherein" insert -- , --

Column 8
Claim 17, Line 15, after "1" and before "wherein" insert -- , --

Column 8
Claim 18, Line 18, after "1" and before "wherein" insert -- , --

Column 8
Claim 19, Line 21, after "1" and before "wherein" insert -- , --

This certificate supersedes the Certificate of Correction issued January 13, 2009.

Signed and Sealed this

Third Day of February, 2009

JOHN DOLL
*Acting Director of the United States Patent and Trademark Office*